(12) United States Patent
Qin et al.

(10) Patent No.: US 12,133,931 B2
(45) Date of Patent: Nov. 5, 2024

(54) BIOACTIVE SCAFFOLD FOR INDUCING TENDON REGENERATION, PREPARATION METHOD THEREFOR AND USE THEREOF

(71) Applicant: WEST CHINA HOSPTIAL, SICHUAN UNIVERSITY, Sichuan (CN)

(72) Inventors: Tingwu Qin, Sichuan (CN); Liangju Ning, Sichuan (CN); Yajing Zhang, Sichuan (CN); Jing Cui, Sichuan (CN); Xuan Yao, Sichuan (CN); Jingcong Luo, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 465 days.

(21) Appl. No.: 16/475,016

(22) PCT Filed: Jun. 15, 2017

(86) PCT No.: PCT/CN2017/088415
§ 371 (c)(1),
(2) Date: Jun. 28, 2019

(87) PCT Pub. No.: WO2018/120672
PCT Pub. Date: Jul. 5, 2018

(65) Prior Publication Data
US 2020/0121828 A1     Apr. 23, 2020

(30) Foreign Application Priority Data

Dec. 28, 2016   (CN) ..................... 201611263819.2

(51) Int. Cl.
*A61L 27/36*        (2006.01)
*A61L 27/38*        (2006.01)

(52) U.S. Cl.
CPC ....... *A61L 27/3662* (2013.01); *A61L 27/3633* (2013.01); *A61L 27/3687* (2013.01);
(Continued)

(58) Field of Classification Search
None
See application file for complete search history.

(56) References Cited

U.S. PATENT DOCUMENTS

| 2012/0178159 A1* | 7/2012 | Ma ...................... C12N 5/0663 435/366 |
| 2013/0123920 A1* | 5/2013 | Sun .................... A61L 27/3625 623/13.11 |
| 2015/0337261 A1* | 11/2015 | Li ...................... A61L 27/3834 424/489 |

FOREIGN PATENT DOCUMENTS

| CN | 101147810 A | 3/2008 | |
| CN | 103966158 * | 5/2014 | ............. C12N 5/071 |

(Continued)

OTHER PUBLICATIONS

Franco-Barraza Curr. Protoc. Cell Biol. 71: 10.9.1-10.9.34, Jun. 2016 (Year: 2016).*

(Continued)

*Primary Examiner* — Evelyn Y Pyla
(74) *Attorney, Agent, or Firm* — NKL Law; Allen Xue

(57) ABSTRACT

Provided is a method of preparing a bioactive scaffold for inducing tendon regeneration, the method includes decellularizing a fresh tendon tissue and to obtain a decellularized tendon sheet scaffold or slice scaffold, and adding ECM materials to the decellularized tendon sheet scaffold or slice scaffold.

1 Claim, 12 Drawing Sheets

(52) U.S. Cl.
CPC ....... *A61L 27/3691* (2013.01); *A61L 27/3834* (2013.01); *A61L 27/3895* (2013.01); *A61L 2430/10* (2013.01); *A61L 2430/40* (2013.01)

(56) References Cited

FOREIGN PATENT DOCUMENTS

| CN | 104208750 A | | 12/2014 | |
|---|---|---|---|---|
| CN | 106075585 A | | 11/2016 | |
| WO | WO 2014/144215 | * | 9/2014 | ............. A61K 35/12 |
| WO | WO 2016/044461 | * | 3/2016 | ............. A61K 35/28 |
| WO | 2017031167 A1 | | 2/2017 | |
| WO | 2017031169 A1 | | 2/2017 | |

OTHER PUBLICATIONS

Omae et al., Journal of Orthopaedic Research, Jul. 2009, pp. 937-942 (Year: 2009).*
Wei et al., J Cell Physiol. Sep. 2012: 227(9): 3216-3224 (Year: 2012).*
Abdallah et al., Cellular & Molecular Biology Letters, vol. 11 (2006) pp. 461-474 (Year: 2006).*
Van Obberghen-Schilling et al., The Journal of Biological Chemistry, vol. 263, No. 16, Issue of Jun. 5, pp. 7741-7746, 1988 (Year: 1988).*
Seghezzi et al., The Journal of Cell Biology, vol. 141, No. 7, Jun. 29, 1998, pp. 1659-1673 (Year: 1998).*
Alberti et al., Advanced Healthcare Materials 2013, 2, 817-821 (Year: 2013).*
Ning Biomaterials, vol. 52, Jun. 2015, pp. 539-550 (Year: 2015).*
Hoshiba et al., Stem Cells International, vol. 16, Article ID 6397820, 10 pages (Year: 2016).*
Joddar et al., Biomater. Sci., 2014, 2, 1595-1603 (Year: 2014).*
Juncosa-Melvin et al., (Tissue Engineering, vol. 12, No. 2, 2006, pp. 369-379) (Year: 2006).*
Liang-Ju Ning et al., "Preparation and characterization of decellularized tendon slices for tendon tissue engineering", Journal of Biomedical Materials Research Part A, Jun. 2012, vol. 100A, Issue 6, pp. 1448-1456.

* cited by examiner

BIOACTIVE SCAFFOLD FOR INDUCING TENDON REGENERATION, PREPARATION METHOD THEREFOR AND USE THEREOF

FIELD OF THE INVENTION

The invention relates to the field of tissue-engineered materials, in particular to a bioactive scaffold for inducing tendon regeneration, and its preparation and use.

BACKGROUND OF THE INVENTION

Tendon defects resulting from diseases, trauma, tissue degeneration, etc. have become an unavoidable health issue. At present, there are various methods to treat or repair tendon defects, including autogenous tendon transplantation, allogenic or xenogenic tendon transplantation, and artificial material repair. An autogenous tendon transplantation, with limited sources for supply, can also trigger pain, infection, and injury at areas where donor tendons come from. While allogenic tendon transplantation, also with limited sources for supply, may cause disease transmission and rejection to various degrees, xenogenic tendon transplantation may cause disease transmission as well. Further, the biggest risk for xenogenic tendon transplantation is immune rejection. On the other hand, artificial material shows poor mechanical compatibility with tendon and has a degradation rate that hardly synchronizes with tendon regeneration. Moreover, artificial material is often expensive and its long-term effect remains to be seen.

An ideal material for tendon repair should meet the following conditions: (1) good biocompatibility; (2) good mechanical compatibility; (3) potential to induce tendon regeneration; (4) controllable shape and size, operable processing and preparation methods. As well-documented, there is a strong need to find better tendon repair materials because the ones currently in use suffers from their own limitations or deficiencies.

With the development of tissue engineering technology, researchers have been encouraged by the prospect of using tissue-engineered tendon to treat or repair tendon defects. With the joint efforts of researchers worldwide, preparing tissue-engineered tendon has made great progress. Still, a number of technical issues linger, which include: supply for stem cells and its associated quantity and quality issues; lack of ideal scaffold materials; how the concentration of exogenous growth factors is controlled when applying to tissue-engineered tendon through sustained release technology; how to solve the synergistic effect and ordering effect for multiple factors; and other yet-to-be-studied problems, e.g., the mechanism of in vitro mechanical stimulation and the optimal stress stimulation conditions. Furthermore, a large-scale application of traditionally engineered tendon needs to rely on its long-term preservation and transportation, which makes the production process time-consuming and costly.

The current tissue-engineered tendon products work far from ideal. They are difficult for preservation and transportation, unsuitable for a more broad clinical application. It appears that the development of tissue-engineered tendon has encountered a technical bottleneck as production by traditional methods cannot meet the clinical goal for tendon defects to be repaired or regenerated.

As shown by an early published study ("Preparation and characterization of decellularized tendon slices for tendon tissue engineering." *Journal of Biomedical Materials Research Part A,* 2012: 100A: 1448-1456) and an issued patent (Patent No. ZL201310636964.0), decellularized tendon slices (DTSs) and decellularized bovine tendon sheets (DBTs) have proven to be excellent scaffolding materials for tissue-engineered tendon. The advantages include: (1) having the scaffolds mainly composed of parallel type I collagen fibers, which has the structure and composition of natural tendon; (2) having a three-dimensional structure unique to tendon and conducive to cell adhesion and proliferation, which provides a good growth environment and facilitates cell-to-scaffold and cell-to-cell communications; (3) removed of cellular components and xenogeneic antigens during processing, significantly reducing antigenicity; (4) retaining basic mechanical strength of tendon; (5) retaining bioactive components in the material as the processing condition is relatively mild; (6) taking advantage of the rich supply from the animal tissue thus eliminating the needs for human tissues and avoiding the issue of limited sources for supply faced by other methods like autogenous or allogenic tendon transplantation.

Nevertheless, the above-described tendon slice and sheet scaffolds, after undergoing a series of physical and enzymatic treatment, still experience partial loss of bioactive factors and show only limited activities in promoting stem cell differentiation in vitro or tendon regeneration in vivo.

Therefore, there is a great need to enhance the biological activities for these tendon slice and sheet scaffolds.

However, with the current method, improvement relies on application of bioactive factors-modified scaffolds. Due to a limited variety of bioactive factors and difficulties in determining a proper concentration for each factor, the results are rather unsatisfactory while the improvement in biological activities is limited.

SUMMARY OF THE INVENTION

In order to solve the above problems, the present invention provides a novel bioactive scaffold that exhibits strong activities in inducing tendon regeneration.

One aspect of this invention relates to a method of preparing a bioactive scaffold for inducing tendon regeneration. The method includes the following steps:

(1) decellularizing a fresh tendon tissue and to obtain a decellularized tendon sheet scaffold or slice scaffold; and (2) adding extracellular matrix (ECM) materials to the decellularized tendon sheet scaffold or slice scaffold.

The method of preparing the decellularized tendon sheet scaffold in the step (1) above is as follows:

(a1) providing a fresh tendon tissue and washing it;

(a2) compressing the tendon tissue along the thickness direction, to reach a compression ratio of 60% to 90% to obtain a tendon sheet;

(a3) freezing and thawing the tendon sheet and repeating the process for 4 to 6 times, wherein the freezing and thawing process is carried out by placing the tendon sheet in liquid nitrogen for 1 to 3 minutes, followed with 3 to 10 minutes at 25 to 37° C.; and (a4) treating the tendon sheet from the step (a3) with nuclease and followed by washing, wherein the nuclease treatment comprises placing the tendon sheet in a solution having DNase at a concentration of 120 to 180 IU/ml and RNase at a concentration of 80 to 120 μg/ml either at room temperature or at 37° C. for 24 hours.

On the other hand, the method of preparing the decellularized tendon slice scaffold in the step (1) above is as follows:
- (b1) providing a fresh tendon tissue and washing it;
- (b2) freezing and thawing the tendon tissue and repeating the process for 4 to 6 times, wherein the freezing and thawing process is carried out by placing the tendon tissue in liquid nitrogen for 1 to 3 minutes, followed with 3 to 10 minutes at 25 to 37° C.;
- (b3) frozen sectioning longitudinally the tendon tissue obtained from the (b2) step, the thickness of the slices being 300-900 μm; and
- (b4) treating the tendon slices from the step (b3) with a nuclease and followed by washing, the nuclease treatment performed by placing the tendon slices in a solution having DNase at a concentration of 120 to 180 IU/ml and RNase at a concentration of 80 to 120 μg/ml either at room temperature or at 37° C. for 24 hours.

In the step (2) above, the adding ECM materials include:
- (c1) preparing a decellularized tendon gel, a process that contains decellularizing, freeze-drying, and pulverizing a tendon tissue to obtain tendon powder, then digesting the tendon powder with a solution having 1 mg/ml of pepsin at room temperature for 24 hours. After neutralization with a base solution, the process further contains placing the digested tendon powder in a PBS solution with a 1:10 volume ratio before developing the treated tendon tissue into a tendon gel in a 37° C. incubator; and
- (c2) pasting the decellularized tendon gel prepared above onto the decellularized tendon sheet or slice scaffold prepared from the step (1) so that the tendon gel completely covers the decellularized tendon sheet scaffold or slice scaffold.

In the step (c1) above, the decellularizing a tendon tissue includes: (i) freezing and thawing the tendon tissue and repeating the process for 4 to 6 times, the freezing and thawing process performed by placing the tendon tissue in liquid nitrogen for 1 to 3 minutes, followed with 3 to 10 minutes at 25 to 37° C.; (ii) frozen sectioning longitudinally the tendon tissue with a slice thickness of 300-900 μm; and (iii) placing the tendon slices in a solution having DNase at a concentration of 120 to 150 IU/ml and RNase at a concentration of 80 to 100 μg/ml in a shaker at 37° C. for 12 hours, followed by neutralizing with 0.2 N NaOH.

In the step (2) above, the adding ECM materials, alternatively, includes:
- (d1) providing tendon cells or stem cells and culturing them on the decellularized tendon sheet scaffold or slice scaffold prepared from the step (1), wherein the stem cells can be bone marrow stromal stem cells, adipose-derived stem cells, or tendon-derived stem cells; and
- (d2) decellularizing the whole cultures after the cultured cells reach 100% confluence. More specifically, when the cultured cells reach 90% confluence, 50 μM vitamin C is added and continue culturing for 6-8 days until the cultured cells form dense cell sheet. Also, the decellularizing the whole cultures includes treatment with 0.5% Triton X-100 containing 20 mM ammonia water at 37° C. for 15 minutes, followed by treatment with 100 U/mL DNase at 37° C. for 2 hours.

Another aspect of the invention provides a bioactive scaffold for inducing tendon regeneration prepared by the foregoing method.

Yet another aspect of the invention also provides the use of the aforementioned bioactive scaffold for inducing tendon regeneration as materials for treating or repairing soft tissue defects. The materials for treating or repairing soft tissue defects also refers to materials for treating or repairing tendon or ligament defects.

Benefits of the present invention include:
(1) The substrate of the prepared bioactive scaffold is composed of a decellularized tendon slice or sheet, and is a natural tendon-derived material;
(2) The prepared bioactive scaffold is subjected to decellularization and antigen removal, thereby effectively reducing the antigenicity of the scaffold;
(3) The prepared bioactive scaffold fully utilizes the ECM components of the tendon tissue, and provides a good microenvironment and mechanical support for the cell, which facilitates cell adhesion, proliferation, and function;
(4) The prepared bioactive scaffold has good mechanical properties, has similar mechanical properties to normal tendon tissues, and can well overcome the problem of poor mechanical compatibility of artificial materials for tendon repair;
(5) The prepared bioactive scaffold has a degradation rate matched with tendon regeneration, and the degradation product is non-toxic and harmless;
(6) The prepared bioactive scaffold is modified by a tendon gel, tendon cell or stem cell ECM, and contains various bioactive factors (Transforming growth factor-β1 (TGF-β1), Insulin-like growth factor-1 (IGF-1), and Vascular endothelial growth factor (VEGF)), structural proteins (Fibronectin, Vitronectin), and proteoglycans (Biglycan, Fibromodulin), etc., which are conducive to the induction of tendon regeneration and repair.
(7) The prepared bioactive scaffold is easy to be adjusted, which is advantageous for suturing and fixing any tendon defects.
(8) The process of preparing the bioactive scaffold of the present invention is simple and fit for large-scale production. The scaffold product is easy to store and transport, with a high added-on value.

In summary, the bioactive scaffold for inducing tendon regeneration, deriving ECM from tendon cells, stem cells, and natural tendon tissues, can effectively repair tendon defects and the repair effect is good, and the method is superior to direct applications of growth factors. It presents great prospects for clinical applications.

The details of the invention are set forth in the drawing and description below. Other features, objects, and advantages of the invention will be apparent from the description and from the claims.

BRIEF DESCRIPTION OF THE DRAWINGS

These drawings illustrate certain aspects of some of the embodiments of the present invention, and should not be used to limit or define the invention.

DETAILED DESCRIPTION

Methods are provided for preparing a bioactive scaffold for inducing tendon regeneration.

Aspects of the methods include preparing a decellularized tendon sheet scaffold or slice scaffold and preparing a decellularized tendon gel.

Before the present methods are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

EXAMPLES

Main Materials, Reagents, and Instruments:

Fresh tendon, bone marrow stromal stem cells, tendon-derived stem cells, tendon cells; cell culture medium, nuclease, DNA detection kit; cryostat microtome, $CO_2$ incubator, biomechanical test system, scanning electron microscope, fluorescence microscope, freeze dryer (Christ, Germany), cryogenic ball mill (Retsch, Germany).

Statistical Method:

Statistical analysis and processing of data were performed using SPSS16.0 software package. All data were expressed as mean±standard deviation. The data satisfied with normal distribution, the variance was uniform, and the two-way comparison between groups was performed by one-way ANOVA (Sceffe method). Test standard a was set to be 0.05, ie, the difference was statistically significant at P<0.05.

Example 1, Preparing a Bioactive Scaffold for Inducing Tendon Regeneration

The bioactive decellularized tendon slice scaffold was prepared from Achilles tendon from a canine hind limb by longitudinally sectioning and was further modified by ECM of tendon-derived stem cells. The specific preparation method is as follows:
(1) providing a fresh tendon tissue and wash it; (2) freezing and thawing the tendon tissue and repeating the process for 4 to 6 times, each process carried out by placing the tendon tissue in liquid nitrogen for 1 to 3 minutes, then at 25 to 37° C. for 3 to 10 minutes; (3) frozen sectioning longitudinally the tendon tissue to obtain slices having a thickness of 300 to 900 µm; (4) placing the slices in a solution having DNase at a concentration of 120 to 180 IU/ml and RNase at a concentration of 80 to 120 µm/ml either at room temperature or at 37° C. for 6 to 24 hours. Finally, freeze and disinfect the thus obtained decellularized tendon slice scaffold for future use.

Figure 1:
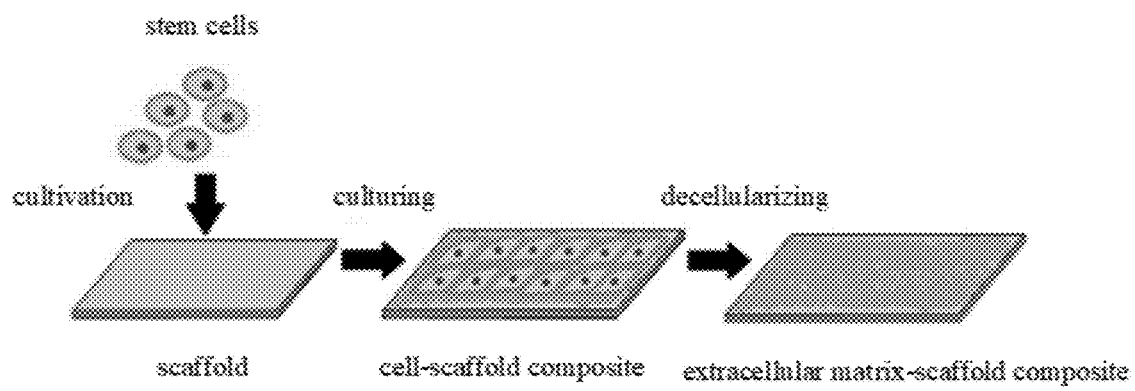
FIG. 1 is a schematic diagram of the preparation process of a bioactive scaffold of the present invention.
Figure 2:
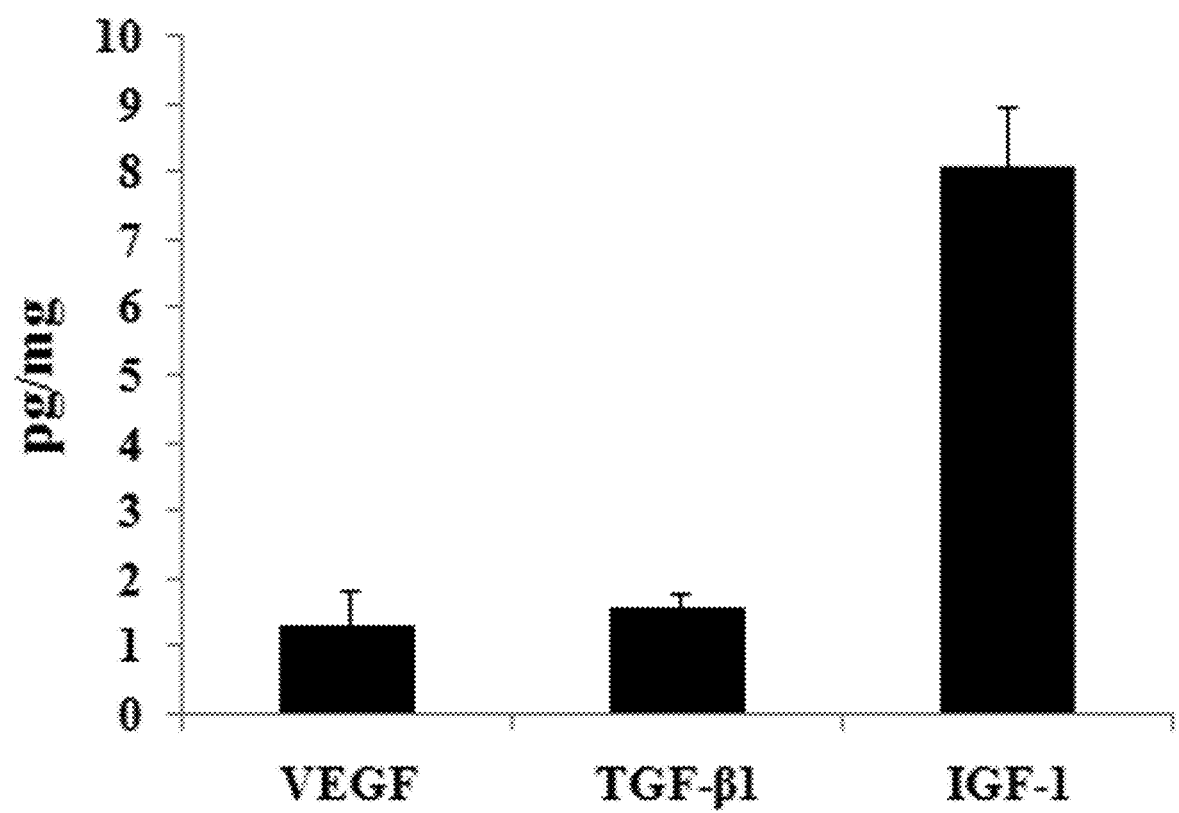
FIG. 2 is a plot showing that a bioactive scaffold of the present invention covered by a tendon gel contains a variety of growth factors.

As shown in FIG. 1, rat tendon-derived stem cells were cultured with the tendon slice scaffold for 7 days, the culture conditions being 5% $CO_2$ and at 37° C. When the cells reached 90% confluence, 50 µM vitamin C was added for additional 8 days until the cells form dense cell sheet on the surface of the tendon slice scaffold. The whole cultured composite was then subjected to decellularization treatment, first treated with 0.5% Triton X-100 containing 20 mM ammonia water at 37° C. for 15 minutes, and then treated with 100 U/ml DNase at 37° C. for 2 hours.

That the cells were completely removed was confirmed by DNA quantification and histological observation. The ECM of tendon-derived stem cells was preserved on the tendon slice scaffold, thus achieving modification by the ECM materials. Compared to a simple tendon slice, the ECM-modified tendon slice scaffold of this invention is a better bioactive scaffold for repairing tendon defects and reconstructing tendon function.

Example 2, Preparing a Bioactive Scaffold for Inducing Tendon Regeneration

The bioactive decellularized tendon sheet scaffold was prepared from bovine Achilles tendon by compressing, decellularizing, and was further modified by the ECM of tendon-derived stem cells. The preparation method was based on the method of claim 1 of Patent No.: ZL201310636964.0. The specific preparation method is as follows:
(1) providing a fresh tendon tissue and wash it; (2) compressing the tendon tissue along the thickness direction to reach a compression ratio of 60% to 90% and obtaining a tendon sheet with a thickness of about 1.0-1.2 mm; (3) freezing and thawing the tendon sheet and repeating the process for 4 to 6 times, each process carried out by placing the tendon sheet in liquid nitrogen for 1 to 3 minutes, followed by at 25 to 37° C. for 3 to 10 minutes; and (4) placing the tendon sheet in a solution having DNase at a concentration of 120 to 180 IU/ml and RNase at a concentration of 80 to 120 µm/ml either at room temperature or at 37° C. for 6 to 24 hours; then the obtained decellularized tendon sheet scaffold freeze-dried and disinfected for use.

As shown in FIG. 1, passage 3 rat tendon-derived stem cells were cultured with the decellularized tendon sheet scaffold obtained above for 7 days, the culture conditions being 5% $CO_2$ and at 37° C. When the cells reached 90% confluence, 50 µM vitamin C was added for additional 8 days until the cells form dense cell sheet on the surface of the decellularized tendon sheet scaffold. The whole cultured composite was then subjected to decellularization treatment, first treated with 0.5% Triton X-100 containing 20 mM ammonia water at 37° C. for 15 minutes, and then treated with 100 U/ml DNase at 37° C. for 2 hours.

It was confirmed by DNA quantification and histological observation that the stem cells had been completely removed, and the ECM of tendon-derived stem cells was preserved on the decellularized tendon sheet scaffold. Compared to other tendon scaffold, the ECM of tendon-derived stem cells modified decellularized tendon sheet scaffold of this invention is a better bioactive scaffold for repairing tendon defects and reconstructing tendon function.

Example 3, Preparing a Bioactive Scaffold for Inducing Tendon Regeneration

1. Preparation Method

Bovine Achilles tendon was used to prepare a bioactive decellularized tendon sheet scaffold. Also, tendon gel was prepared. The preparation method was based on the method of claim 1 of Patent No.: ZL201310636964.0. The decellularized tendon sheet scaffold thus obtained was applied for repairing the Achilles tendon defects and reconstructing the Achilles tendon function on a rabbit. The specific preparation and use methods are as follows:

First, preparation of a decellularized tendon sheet scaffold: (1) providing a fresh tendon tissue and wash it; (2) compressing the tendon tissue along the thickness direction to reach a compression ratio of 60% to 90% and obtaining a tendon sheet with a thickness of about 1.0-1.2 mm; (3) freezing and thawing the tendon sheet and repeating the process for 4 to 6 times, each process carried out by placing the tendon sheet in liquid nitrogen for 1 to 3 minutes, followed by at 25 to 37° C. for 3 to 10 minutes; and (4) placing the tendon sheet in a solution having DNase at a concentration of 120 to 180 IU/ml and RNase at a concentration of 80 to 120 µm/ml either at room temperature or at 37° C. for 6 to 24 hours; then the obtained decellularized tendon sheet scaffold freeze-dried and disinfected for use.

Next, preparation of a tendon gel: a fresh tendon tissue from rhesus macaques was decellularized by: (i) freezing and thawing the tendon tissue and repeating the process for 4 to 6 times, each process performed by placing the tendon tissue in liquid nitrogen for 1 to 3 minutes, followed by at 25 to 37° C. for 3 to 10 minutes; (ii) frozen sectioning longitudinally the tendon tissue into slices of 300-900 µm thick; and (iii) placing the slices in a solution having DNase at a concentration of 120 to 150 IU/ml and RNase at a concentration of 80 to 100 µg/ml in a shaker at 37° C. for 12 hours, followed by freeze-drying at −80° C. and ball milling at −20° C. to obtain tendon powder; (iv) digesting the tendon powder in a 1 mg/ml pepsin solution at room temperature for 24 hours, then neutralized with 0.2 N NaOH, and placing the digested tendon powder in a PBS solution with a 1:10 volume ratio before putting in a 37° C. incubator to develop into a tendon gel.

The decellularized tendon gel prepared above was combined with the rehydrated decellularized bovine tendon sheet scaffold also prepared above by pasting the tendon gel on the surface of the decellularized bovine tendon sheet scaffold so that the former completely covered the latter.

Adult white rabbits were used to prepare an animal model of bilateral Achilles tendon defects in the hind limb. The decellularized bovine tendon sheet scaffold was applied to repair the tendon and to reconstruct the tendon function. After the operation, gross, histological, imaging, biomechanical tests confirmed that the bioactive decellularized bovine tendon sheet scaffold showed the effect of inducing tendon regeneration and recovering the tendon function. The detailed repair experiment and results are shown in Experimental Example 1 below.

2. Testing

Tissue lysate (FNN0071, Invitrogen; gel mass/tissue lysate volume=1 g/10 ml) was added to the tendon gel, mixed, and the mixture was placed in ice bath for 1.5 hours. The homogenate was centrifuged at 10,000 g for 20 minutes at 4° C., and the supernatant was taken for testing. An ELISA assay was performed according to the instructions of VEGF, TGF-β1 and IGF-1 detection kits, respectively.

The results of ELISA showed that the tendon gel contained growth factors associated with tendon repair, VEGF, TGF-β1, and IGF-1 being 1.30±0.53 pg/mg, 1.56±0.24 pg/mg, and 8.07±0.89 pg/mg, respectively.

The beneficial effects of the present invention will be described below by way of experimental examples.

Experimental Example 1. Properties of Bioactive Scaffolds of this Invention in Inducing Tendon Regeneration 1. Experimental Method The bioactive scaffold prepared according to the method of Example 1 was tested for its properties as follows:
(1) Bioactive Scaffold Histological Examination H&E staining, Masson staining, and DAPI staining were performed according to the method described in the literature: Ning L J, et al. Preparation and characterization of decellularized tendon slices for tendon tissue engineering. Journal of Biomedical Materials Research Part A, 2012: 100A: 1448-1456.
(2) Surface Morphology Observation Surface morphology was observed using a scanning electron microscope (SEM). The specific procedure included: fixing samples to be tested (control group and experimental group) with 2.5% glutaraldehyde at 4° C. for more than 2 hours; washing in PBS for 30 minutes×3 times; followed by alcohol-based gradient dehydration at 50%, 70%, 80%, 90%, 100% each for 15 minutes and critical point drying. Finally, scanning electron microscopy was conducted after vacuum gold spraying.
(3) Growth Factor Detection Same as the ELISA detection method discussed above, follow the instructions of the growth factor test kits.
(4) Observation of Cell Compatibility Same as scanning electron microscope (SEM) observation method discussed above. Samples included the decellularized tendon slice scaffolds with ECM modification by tendon-derived stem cells and scaffolds without the modification, both of them being surface-seeded with BMSCs. The sample processing method was the same as above.
(5) Western blot quantitative detection of ECM protein content changes before and after ECM modification of the decellularized tendon slice scaffolds by tendon-derived stem cells. The procedure for western-blot quantitative detection of ECM protein content in bioactive scaffolds included: extraction of total proteins in the scaffolds to be tested; total protein content of all protein samples using BCA protein concentration determination kit (following the instructions); Electrophoresis and antibody incubation of active scaffold-related proteins (Biglycan, Fibromodulin, Fibronectin and Vitronectin); Gray-scale analysis of protein bands using Gel-Pro Analyzer4 software; relative expression of target proteins in all samples was normalized by each sample's internal reference, namely, the relative expression amount of the target protein=the gray value of the target protein/the gray value of the GAPDH.
(6) AlamarBlue® quantitative detection of effects on proliferation of BMSCs by the bioactive scaffolds that are modified by ECM of tendon-derived stem cells. Detection was carried out according to the method described in the literature: Ning L J, et al. Preparation and characterization of decellularized tendon slices for tendon tissue engineering. Journal of Biomedical Materials Research Part A, 2012: 100A: 1448-1456.
(7) Live/Dead Cell Staining The surface of the decellularized tendon slice and the bioactive decellularized tendon sheet scaffold was incubated overnight in serum-free DMEM medium. BMSCs were seeded on the surface of the scaffold, and, after culturing at 5% $CO_2$ and 37° C., live cells were stained for viability test on the first and third day: first, washing 3 times in sterile PBS; then incubated in a viability dye solution (1 ml sterile PBS+1 μl calcein acetoxymethylester+1 μl propidiumiodide) at 37° C. for 30 minutes in the dark. Finally, the cells were washed 3 times with sterile PBS and observed by fluorescence microscopy.

2. In Vivo Repair Experiments

The composite material prepared in Example 3 above (in which the thickness of the tendon gel covering the decellularized bovine tendon sheet scaffold was 100 to 300 μm) was applied to an in vivo repair experiment as follows: 63 male adult New Zealand white rabbits were randomly selected into 3 groups: a blank group (as a control group), a simple decellularized bovine tendon sheet group (DBTs), and the composite group including the tendon gel and decellularized bovine tendon sheet (ECM+DBTs). An Achilles tendon defect model was prepared measuring 2 cm defect on the Achilles tendon (FIG. 10), and the model was tested by the treatment group to repair the Achilles defects. The blank group underwent primary repair after the Achilles tendon was cut. After the operation, B-ultrasound and MRI were performed on the 4th, 8th, and 12th week, and further histological analysis (H&E staining) and biomechanical testing were performed.

Figure 11:
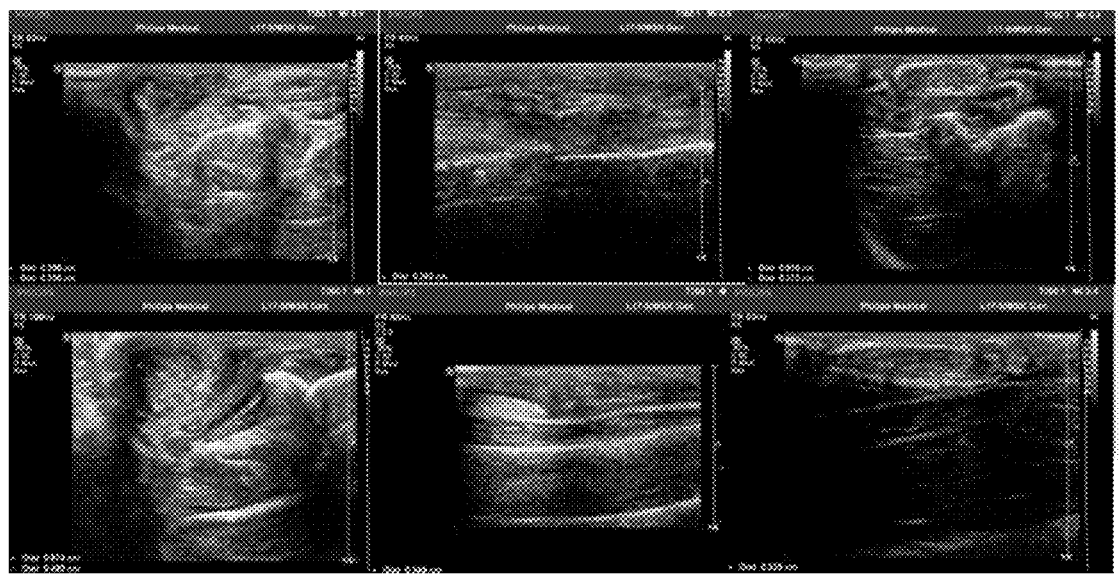
FIG. 11 is images from ultrasound observations of different groups at different time points after surgery.
Figure 12:
FIG. 12 is images for MRI observations of different groups at different time points after surgery. B-ultrasound and MRI tests were performed on rabbit Achilles tendon at 4, 8, and 12 weeks after operation. It was found that the abnormal echo and abnormal signals in the three groups of repaired and reconstructed Achilles tendon were reduced with time. The bioactive scaffold was obviously subjected to shape change. It is gradually remodeled to the same signal as the autogenous Achilles tendon, and at the 12th week, the difference between the groups of autogenous tendon and the bioactive scaffold of this invention cannot be distinguished.
Figure 13:
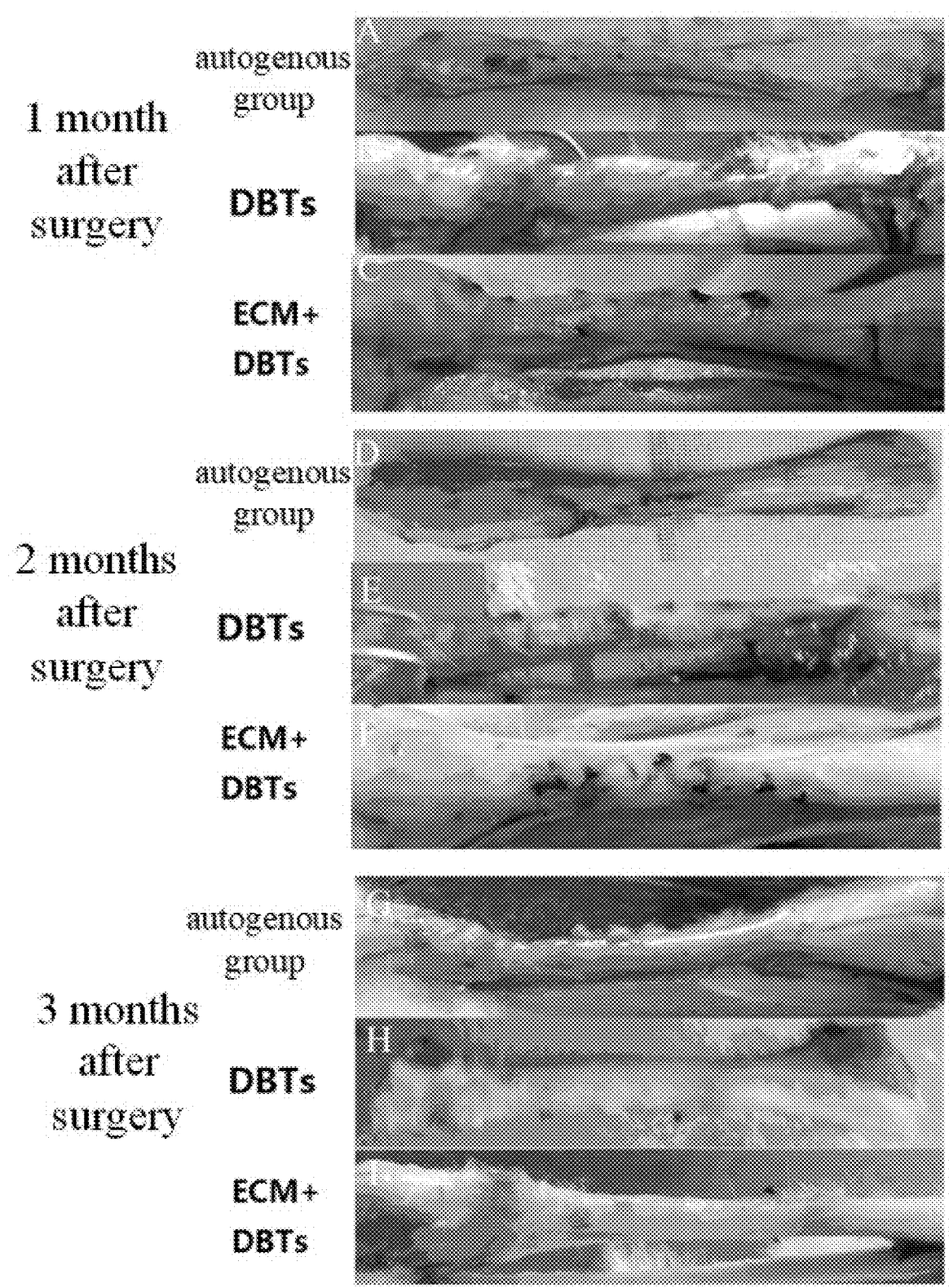
FIG. 13 is images for a general observation of different groups at different time points after surgery.
Figure 14:
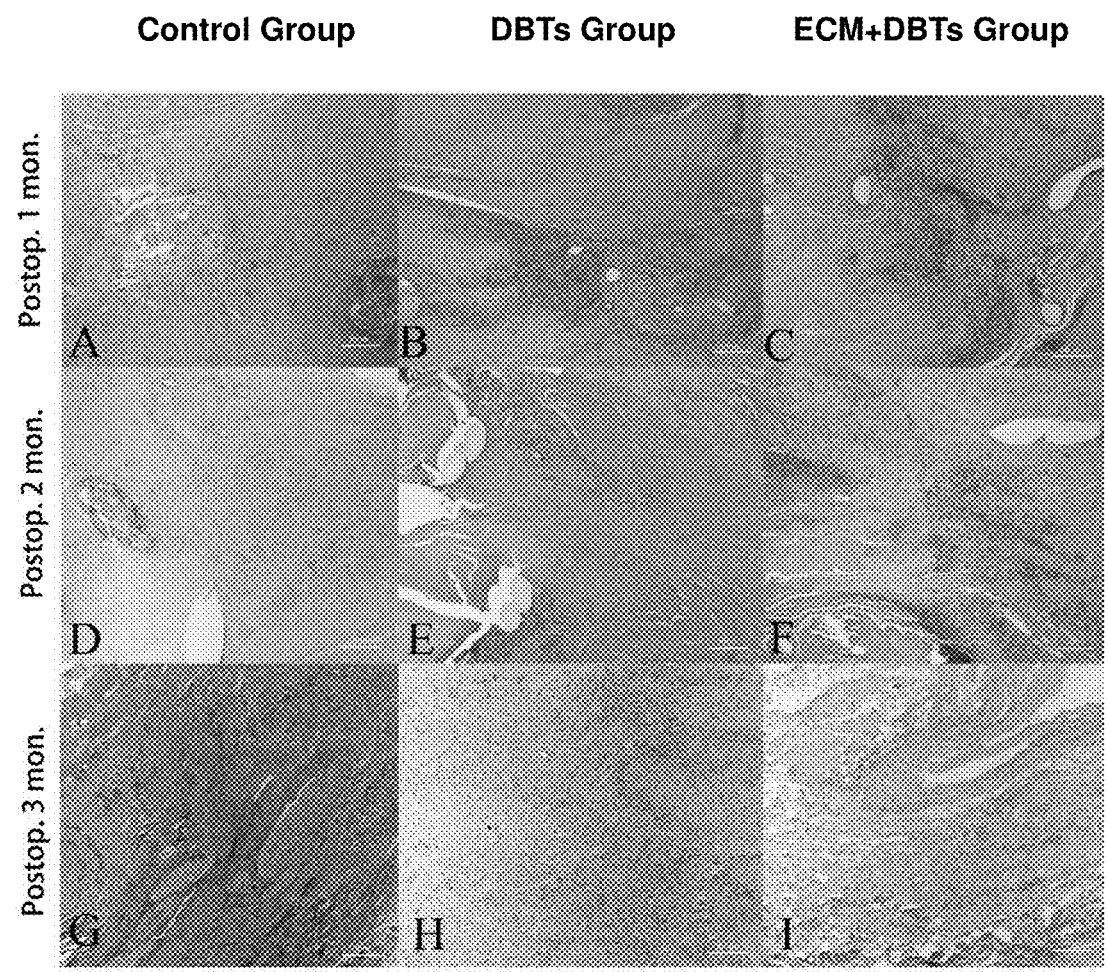
FIG. 14 is images showing histological (H&E staining) observations of different groups at different time points after surgery. Gross and histological observations showed that the scar tissue formed in the defect sites repaired by autogenous tendon and decellularized bovine tendon sheet, and the inflammatory reaction around the decellularized bovine tendon sheet was obvious at 4 weeks; the bioactive scaffold group was followed by the 12 weeks postoperatively. The defect has been reconstructed, the fiber bundles were continuous, and the inflammatory response was significantly reduced. DBTs are decellularized bovine tendon sheet scaffolds and ECM is a tendon gel.
Figure 15:
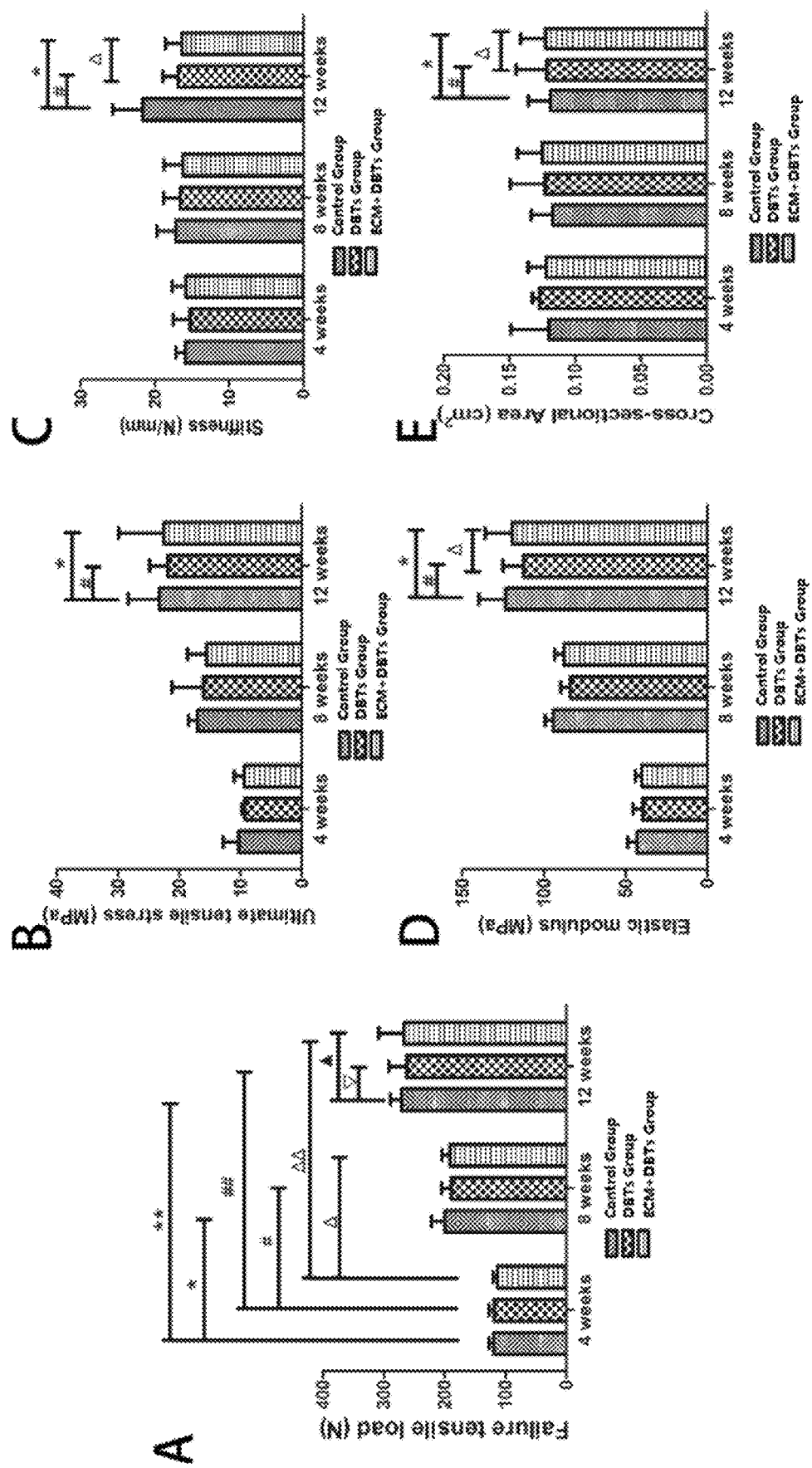
FIG. 15 is plots for biomechanical testing of Achilles tendon repaired with bioactive scaffolds at different times after surgery. The results showed that the maximum load and stiffness of the experimental group increased gradually with time. There was no significant difference in the maximum load between the control group and the bioactive scaffold group at 12 weeks (P>0.05). The maximum load and stiffness of the tendon sheet group and the tendon gel-modified tendon sheet group were higher than those of the control group at 4 weeks (P<0.05). DBTs are decellularized bovine tendon sheet scaffolds and ECM is a tendon gel.

Results: B-ultrasound and MRI were performed on rabbit Achilles tendon at 4, 8, and 12 weeks after the operation. It was found that with the three groups of repaired and recovered Achilles tendon, their abnormal echo and abnormal signals decreased with time. The Achilles tendon in the composite group, after recovery, showed signals the same as that of the autogenous Achilles tendon. Any difference between the tendon repaired by the composite (having the tendon gel and decellularized bovine tendon sheet scaffold) and the autogenous tendon could not be distinguished at the 12th week (FIG. 11 and FIG. 12). Three sets of specimens were taken for general observation (FIG. 13), histological observations, and biomechanical tests. Gross and histological observations showed in the control group and simple decellularized bovine tendon sheet scaffold group, scar tissues were formed at the 4th week, and there was clear inflammatory reaction around the simple decellularized bovine tendon sheet scaffold. By contrast, in the composite group at the 12th week, the Achilles tendon defect had been repaired, the fiber bundles were continuous, and the inflammatory response was significantly reduced (FIGS. 13 and 14). The results of biomechanical tests showed that the maximum load and stiffness in the three groups increased gradually with time. There was no significant difference in the maximum load between the control group and the composite group at the 12th week (P>0.05). At the 4th week, the maximal load and stiffness in the control group were higher than those of the simple decellularized bovine tendon sheet scaffold group and the composite group (P<0.05) (FIG. 15).

3. Experimental Results

Figure 3:
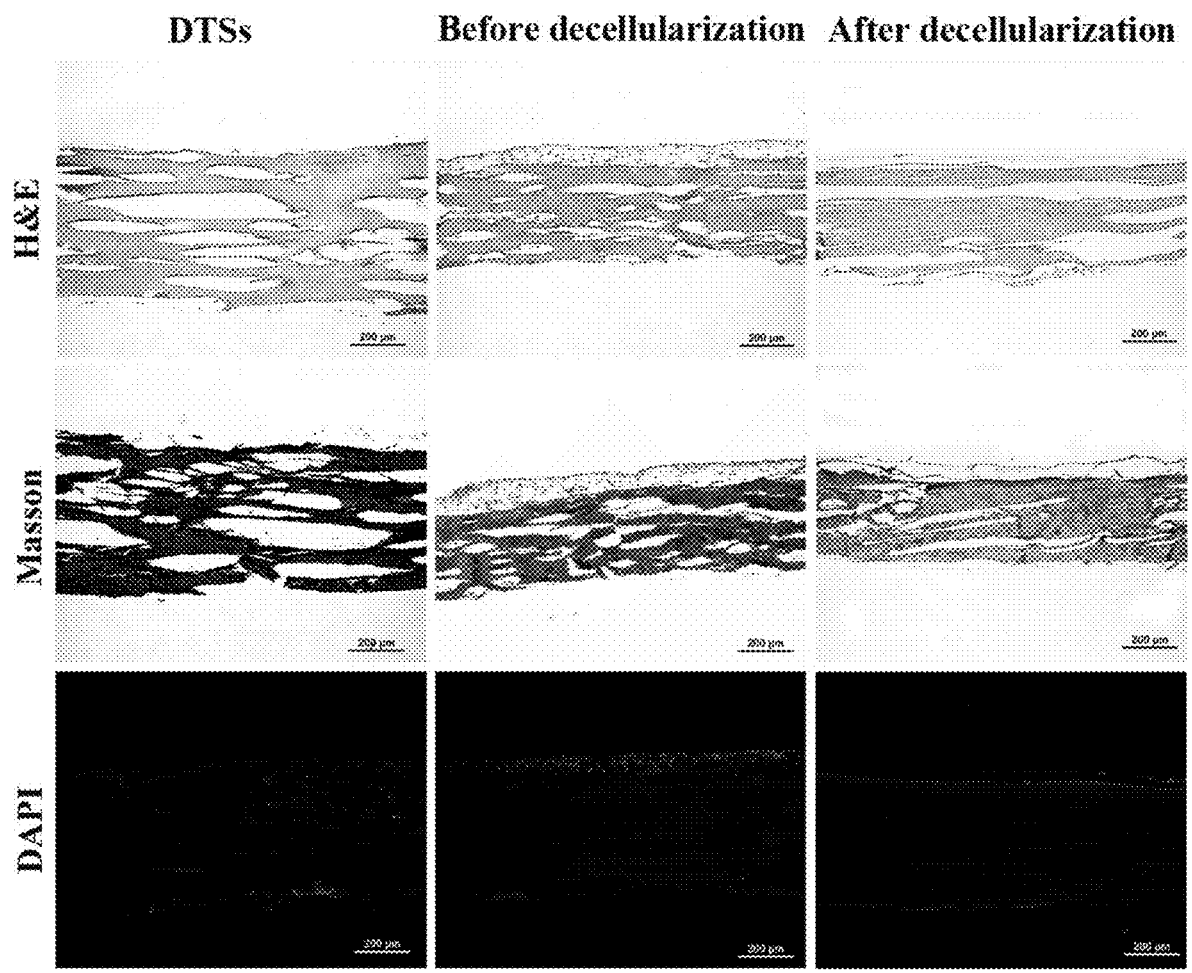
FIG. 3 contains images of H&E staining showing histology of bioactive scaffolds of the present invention after modification by the ECM of tendon-derived stem cells: Masson staining and DAPI staining confirmed that cell fractions were effectively removed by decellularization, while ECM components were retained on the surface of the decellularized tendon sheet scaffold. DTSs stand for decellularized tendon slices.

As shown in FIG. 3, H&E staining, Masson staining, and DAPI staining confirmed that the decellularization treatment effectively removed the stem cells while retaining the ECM component on the surface of the decellularized tendon slice scaffold. DTSs stand for decellularized tendon slices.

Figure 4:
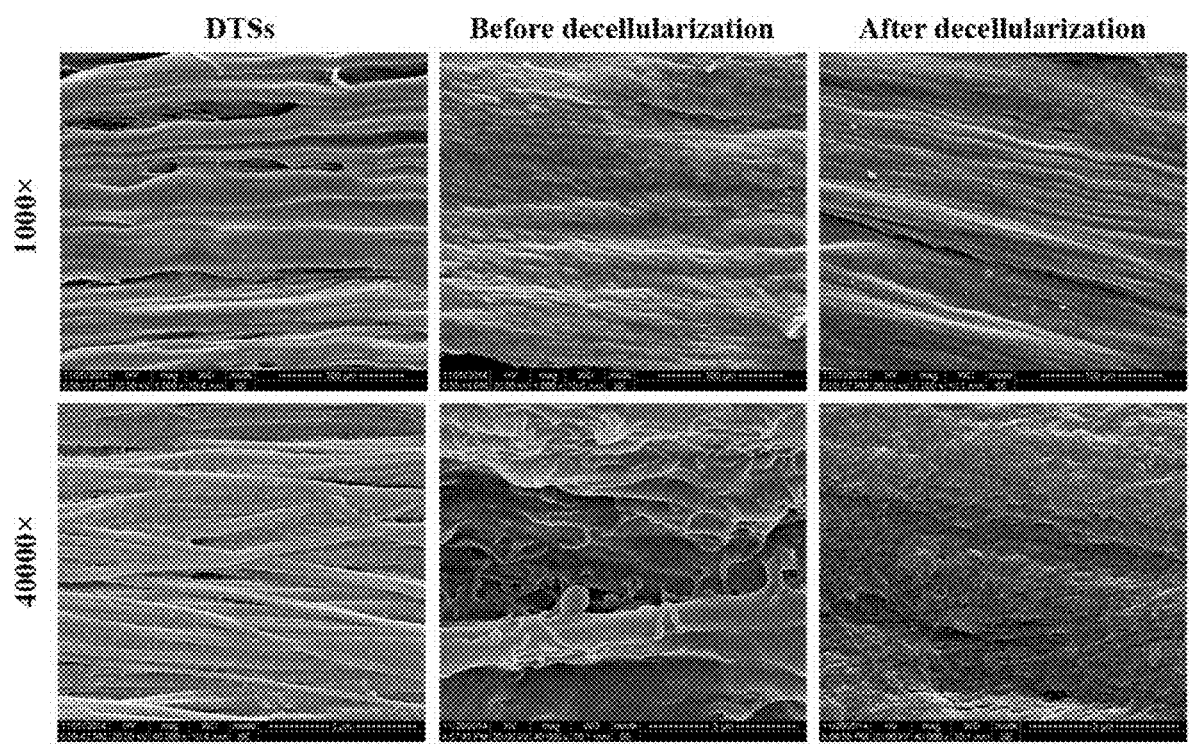
FIG. 4 is images for observation of the surface morphology of bioactive scaffolds of the present invention: The tendon-derived stem cells were cultured on the surface of the tendon slice to form a cell-scaffold composite. After decellularization, the surface of the scaffolds showed a large amount of stem cell ECM deposition. DTSs in the figure stand for decellularized tendon slices.

As shown in FIG. 4, tendon-derived stem cells were cultured on the surface of the tendon slice scaffold to form a cell-scaffold composite, and after decellularization treatment, a large amount of ECM deposition left by the tendon-derived stem cells was observed on the surface of the decellularized tendon slice scaffold. The DTSs in the figure refer to decellularized tendon slices.

Figure 5:
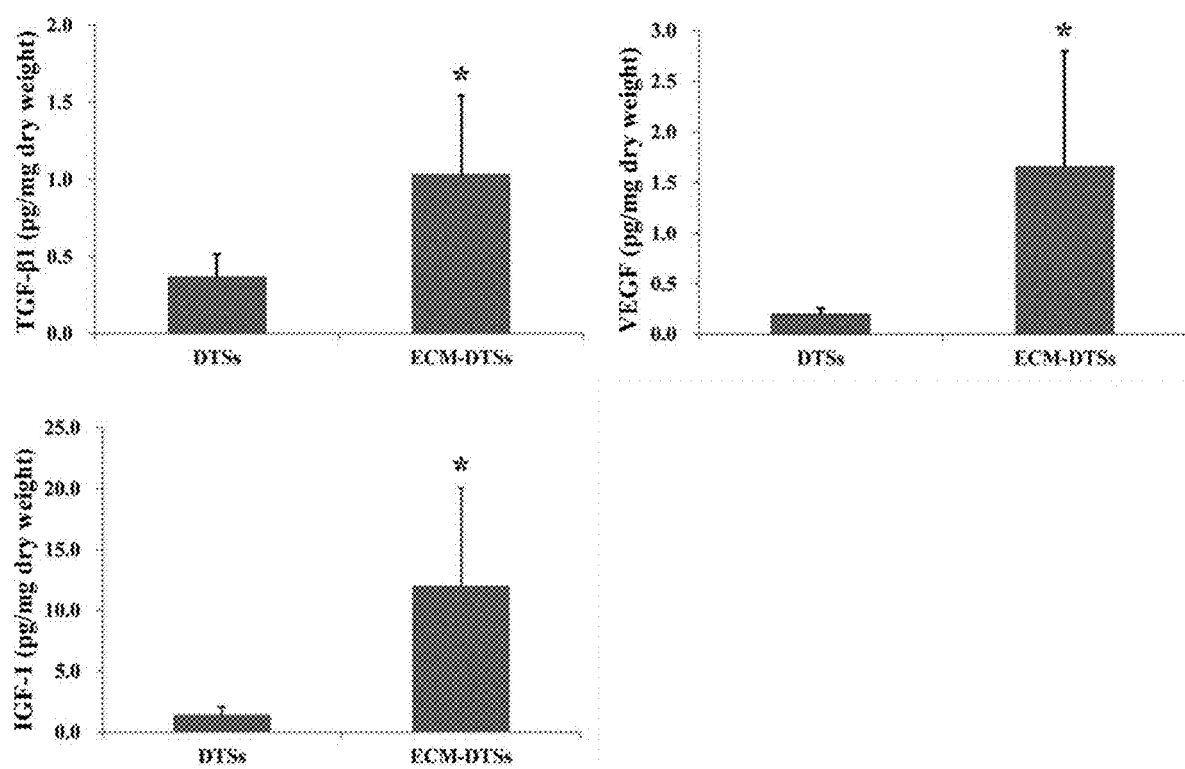
FIG. 5 is plots showing growth factors assay of decellularized tendon slice scaffolds modified by the ECM of tendon-derived stem cells of the present invention: ELISA quantitative results showed that the growth factor (TGF-β1, VEGF and IGF-1) levels in the bioactive scaffolds after ECM modification by tendon-derived stem cells were significantly increased. In the figure, DTSs refer to decellularized tendon slices, and ECM-DTSs are bioactive scaffolds modified by ECM of tendon-derived stem cells.

As shown in FIG. 5, the ELISA quantitative results showed that the growth factor (TGF-β1, VEGF, and IGF-1) levels in the bioactive scaffolds modified by ECM of tendon-derived stem cells were significantly increased. In the figure, DTSs stand for decellularized tendon slices, and ECM-DTSs refer to bioactive scaffolds modified by ECM of tendon-derived stem cells.

Figure 6:
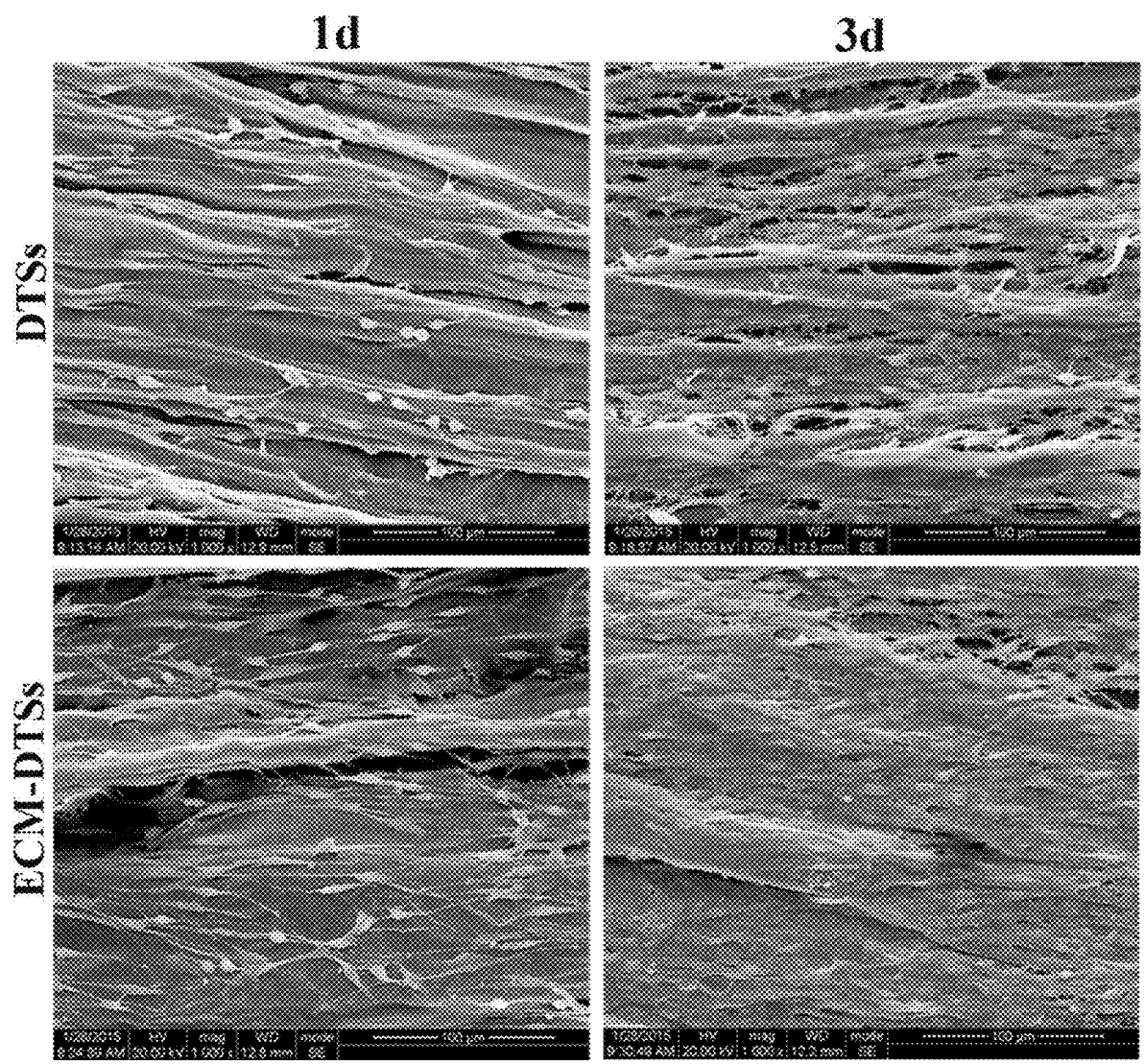
FIG. 6 is plots for cytocompatibility of ECM modified decellularized tendon slice scaffolds of the present invention: SEM analysis confirmed that the surface of ECM modified bioactive scaffolds is suitable for the growth of bone marrow stromal stem cells (BMSCs) with good cell compatibility. In the figure, DTSs stand for decellularized tendon slices, and ECM-DTSs are bioactive scaffolds modified by ECM of tendon-derived stem cells.

As shown in FIG. 6, SEM examination confirmed that the surface of the bioactive scaffold modified by ECM of tendon-derived stem cells is suitable for the growth of BMSCs and has good cell compatibility. In the figure, DTSs refer to decellularized tendon slices, and ECM-DTSs stand for bioactive scaffolds modified by ECM of tendon-derived stem cells.

Figure 7:
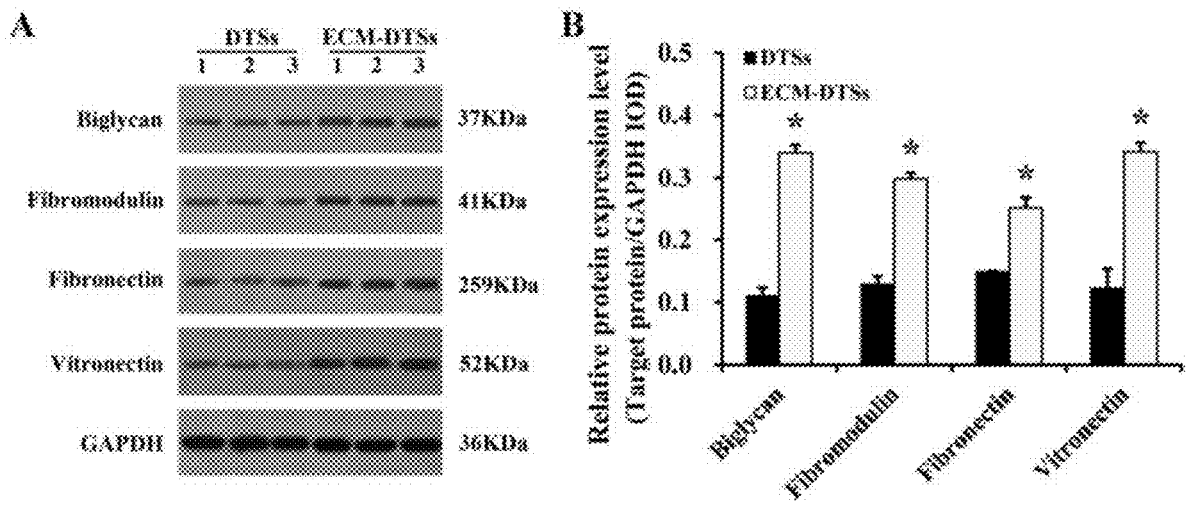
FIG. 7 is graphs of western-blot quantitative detection of ECM protein content before and after modification by tendon-derived stem cell ECM in decellularized tendon slice scaffolds of the present invention. The results showed that the content of ECM protein components (Biglycan, Fibromodulin, Fibronectin and Vitronectin) in the bioactive scaffolds modified by ECM of tendon-derived stem cells was significantly increased. In the figure, DTSs stand for decellularized tendon slices, and ECM-DTSs are bioactive scaffolds modified by ECM of tendon-derived stem cells. * indicates a significant difference compared to the DTSs group.

As shown in FIG. 7, the results showed that the content of ECM protein components (Biglycan, Fibromodulin, Fibronectin, and Vitronectin) in the bioactive scaffold modified by ECM of tendon-derived stem cells was significantly increased. In the figure, DTSs refer to decellularized tendon slices, and ECM-DTSs are bioactive scaffolds modified by ECM of tendon-derived stem cells. * indicates a significant difference compared to the DTSs group.

Figure 8:
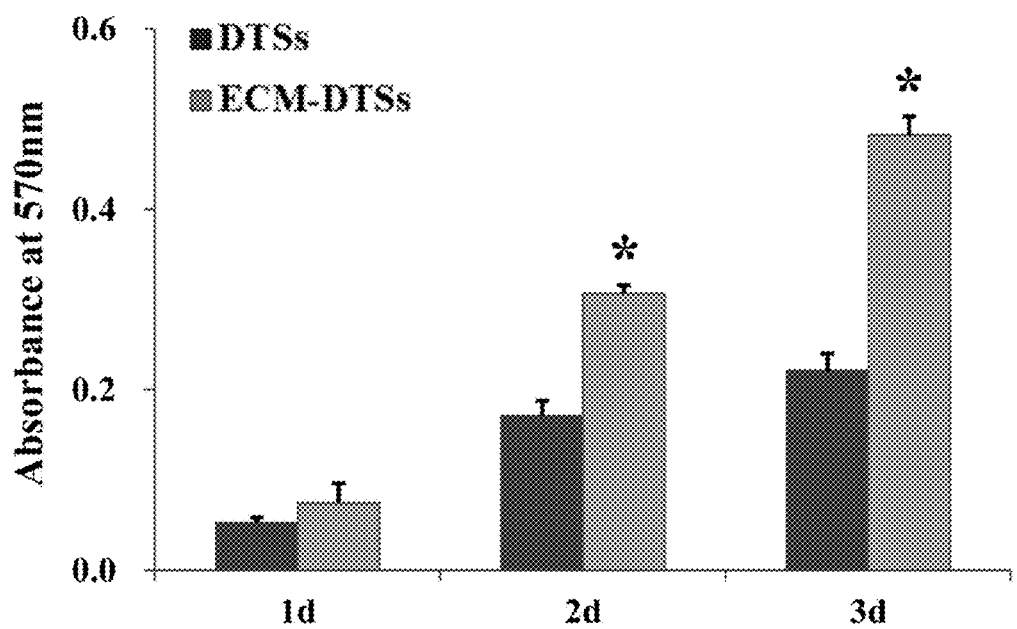
FIG. 8 is images of AlamarBlue® quantitatively detects the effect of bioactive scaffolds obtained from ECM of tendon-derived stem cells modified decellularized tendon slices on the proliferation of BMSCs. In the figure, DTSs refer to decellularized tendon slices, and ECM-DTSs are bioactive scaffolds modified by ECM of tendon-derived stem cells. * indicates a significant difference compared to the DTSs group.

As shown in FIG. 8, the DTSs in the figure stand for decellularized tendon slices, and the ECM-DTSs refer to bioactive scaffolds modified by the ECM of tendon-derived stem cells. * indicates a significant difference compared to the DTSs group.

Figure 9:
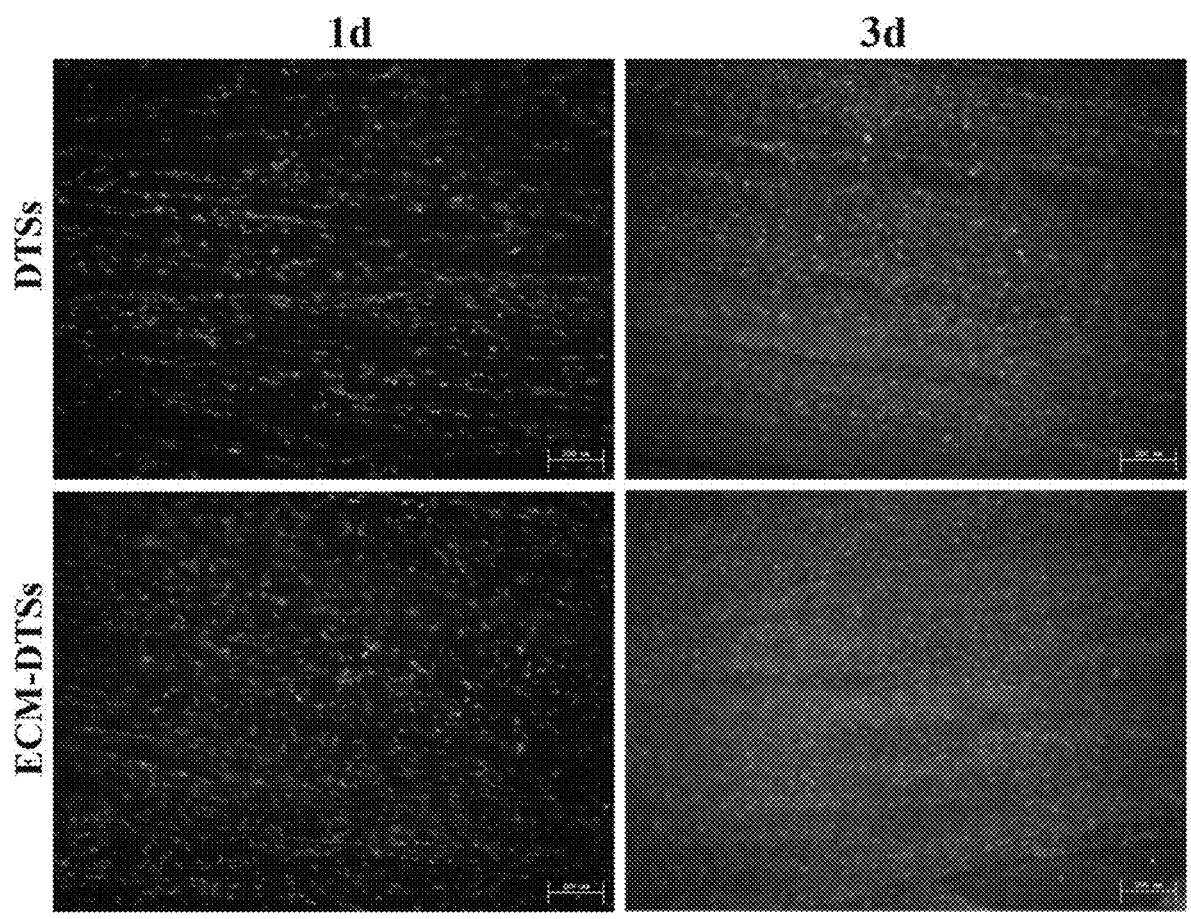
FIG. 9 is images of live/dead cell staining results showed that BMSCs maintained higher cell viability on the ECM modified bioactive scaffold of tendon-derived stem cells. In the figure, DTSs are decellularized tendon slices, and ECM-DTSs are bioactive scaffolds modified by ECM of tendon-derived stem cells.

As shown in FIG. 9, Live/Dead cell staining showed that BMSCs maintained higher cell viability on the bioactive scaffold that was ECM modified by tendon-derived stem cells. In the figure, DTSs refer to decellularized tendon slices, and ECM-DTSs are bioactive scaffolds modified by ECM of tendon-derived stem cells.

Figure 10:
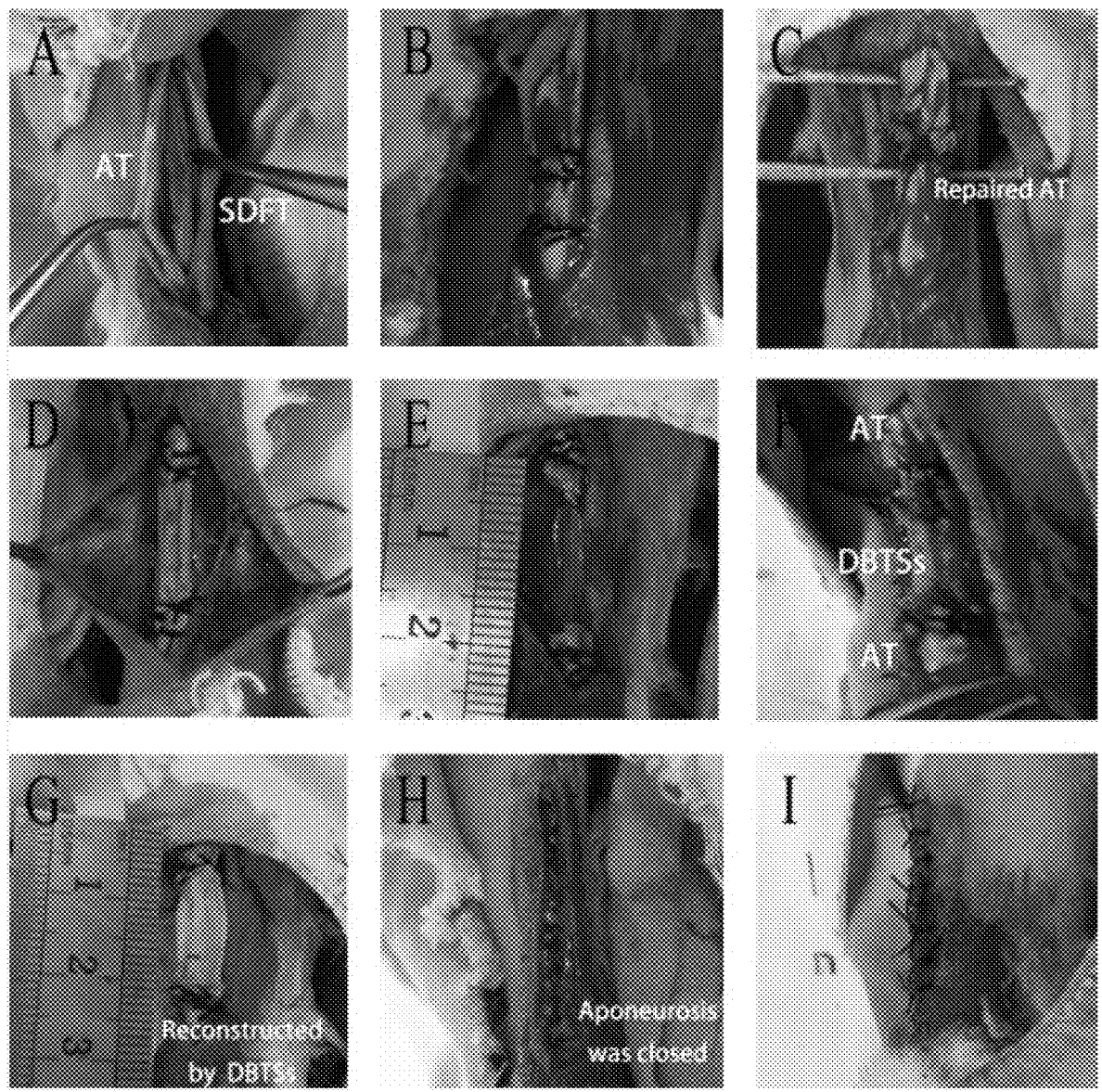
FIG. 10 is images for construction and surgical repair of a rabbit Achilles tendon defect model. SDFT is superficial flexor tendon, DBTs are decellularized bovine tendon sheets, and AT is Achilles tendon.

As shown in FIG. 10, the rabbit Achilles tendon defect model was reconstructed and surgically repaired. SDFT is superficial flexor tendon, DBTs are decellularized bovine tendon sheet, and AT is Achilles tendon.

As shown in FIG. 11, ultrasound observations of different groups at different weeks after the surgical operation; as shown in FIG. 12, MiII observations of different groups at different weeks after the surgical operation. B-ultrasound and MiII tests were performed on rabbit Achilles tendon at 4, 8, and 12 weeks after operation. It was found that the abnormality of echo and abnormal signals of the three groups of repaired and reconstructed Achilles tendon decreased with time; the composite group having the bioactive scaffold was obvious in appearance. It was gradually remodeled and had the same signal as the autogenous Achilles tendon. At the 12th week, it was impossible to distinguish the difference between the tendon tissues repaired by the autogenous tendon and by the composite group.

As shown in FIG. 13, the different groups were observed at different weeks after the surgical operation; as shown in FIG. 14, histology (H&E staining) of different groups at different weeks was observed. Gross histological observation showed images of the autogenous tendon and that in the decellularized bovine tendon sheet group (DBTs). Scar tissue was formed at the 4th week, and the inflammatory reaction around the decellularized bovine tendon sheet was visible. At the 12th week, the Achilles tendon defects in the composite group (ECM+DBTs) were repaired or had been recovered; the fiber bundles were continuous, and the inflammatory response was significantly reduced. DBTs stand for decellularized bovine tendon sheet and ECM refers to tendon gel.

As shown in FIG. 15, biomechanical test of the repaired Achilles tendons was performed at different time points after the surgical operation. The results showed that the maximum load and stiffness of the experimental group increased gradually with time. There was no significant difference in the maximum load between the control group and the composite group at the 12th week (P>0.05). At the 4th week, the maximal load and stiffness in the control group were higher than those of the simple decellularized bovine tendon sheet group and the composite group (P<0.05). DBTs are decellularized bovive tendon sheets and ECM refers to tendon gel.

In summary, the bioactive scaffold obtained by the method of this invention for inducing tendon regeneration exhibited high growth factor content, good biocompatibility, excellent in vivo repairing effects, and thus has good prospect for clinic applications.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a cell-free bioactive scaffold for inducing tendon regeneration, comprising:
   (1) decellularizing a fresh tendon tissue and to obtain a decellularized tendon sheet scaffold, wherein the decellularized tendon sheet scaffold has one single tendon sheet; and
   (2) adding tendon gel extracellular matrix (ECM) to the decellularized tendon sheet scaffold,
   whereby the decellularized tendon sheet scaffold thus obtained is capable of repairing an Achilles tendon defect in 12 weeks,
   wherein the cell-free bioactive scaffold is planar in shape is formed by the decellularized tendon sheet scaffold, wherein the adding tendon gel ECM comprises:
(d1) preparing a decellularized tendon gel, comprising: (i) decellularizing, freeze-drying, and pulverizing a tendon tissue to obtain tendon powder; (ii) digesting the tendon powder with pepsin; and (iii) placing the digested tendon powder in a PBS solution with a 1:10 volume ratio and then in a 37° C. incubator to form a decellularized tendon gel; and
(d2) pasting the decellularized tendon gel onto the decellularized tendon sheet scaffold prepared from the step (1) so that the tendon gel completely covers the decellularized tendon sheet scaffold,
wherein in the step (d1) above, the decellularizing a tendon tissue includes:
(i) compressing the tendon tissue along a thickness direction thereof to reach a compression ratio of 60% to 90% and obtaining a tendon sheet with a thickness of about 1.0-1.2 mm;
(ii) freezing and thawing the tendon sheet and repeating the process for 4 to 6 times, each process performed by placing the tendon tissue in liquid nitrogen for 1 to 3 minutes, followed with 3 to 10 minutes at 25 to 37° C.; and
(iii) placing the tendon sheet in a solution having DNase at a concentration of 120 to 180 IU/ml and RNase at a concentration of 80 to 120 μg/ml in a shaker at 37° C. for 6 to 24 hours, followed by freeze-drying and disinfection the tendon sheet.

* * * * *